United States Patent
Lee et al.

(10) Patent No.: US 8,658,781 B2
(45) Date of Patent: Feb. 25, 2014

(54) PRIMER SET, METHOD AND KIT FOR DETECTING PATHOGEN IN FISH

(71) Applicant: National Cheng Kung University, Tainan (TW)

(72) Inventors: Gwo-Bin Lee, Tainan (TW); Shih-Chu Chen, Tainan (TW); Tzong-Yueh Chen, Tainan (TW); Wen-Hsin Chang, Tainan (TW); Chih-Hung Wang, Tainan (TW); Ming-An Tsai, Tainan (TW)

(73) Assignee: National Cheng Kung University, Tainan (TW)

( * ) Notice: Subject to any disclaimer, the term of this patent is extended or adjusted under 35 U.S.C. 154(b) by 0 days.

(21) Appl. No.: 13/692,210

(22) Filed: Dec. 3, 2012

(65) Prior Publication Data

US 2013/0149702 A1 Jun. 13, 2013

(30) Foreign Application Priority Data

Dec. 12, 2011 (TW) .............................. 100145819 A

(51) Int. Cl.
*C12Q 1/68* (2006.01)

(52) U.S. Cl.
USPC .................. 536/24.3; 435/6.11; 435/6.12

(58) Field of Classification Search
None
See application file for complete search history.

(56) References Cited

U.S. PATENT DOCUMENTS 5,474,796 A * 12/1995 Brennan ................ 427/2.13

OTHER PUBLICATIONS

Office Action issued by Taiwan Intellectual Property Office on Sep. 11, 2013 for corresponding TW Patent Application No. 100145819.

Chang et al. Integrated Microfluidic Loop-Mediated-Isothermal-Amplification Systems for Rapid Isolation and Detection of Aquaculture Pathogens. Solid-State Sensors, Actuators and Microsystems Conference (Transducers), 16th International, Jun. 2011.
Wang et al. An integrated microfluidic loop-mediated-isothermal-amplification system for rapid sample pre-treatment and detection of viruses. Biosensors and Bioelectronics. 26(2011) 2045-2052.
Adams and Thompson, Sci. Technol., Rev.. 2008, p. 197-209, vol. 27.
Chi et al., Dis. Aquat. Organ., 2003, p. 221-228, vol. 55.
Shieh and Chi, Dis. Aquat. Organ., 2005, p. 53-60, vol. 63.
Dhar et al., J. Virol. Methods, 2002, p. 69-82, vol. 104.
Nishizawa et al., J. Gen. Virol. , 1995, p. 1563-1569, vol. 76.
Dallavalle et al., Vet. Microbiol., 2005, p. 167-179, vol. 110.
Grotmol et al., Dis. Aquat. Organ., 2000, vol. 39, p. 79-88.
Mori et al., Biochem. Biophys. Res. Commun., 2001, vol. 289, p. 150-154.
Tomita et al., Nat. Protoc., 2008, vol. 3, p. 877-882.
Piepenburg et al., PLoS Biol., 2006, vol. 4, p. e204.
Starkey et al., Dis. Aquat. Organ., 2004, vol. 59, p. 93-100.
Walker et al., Nucleic Acids Res., 1994, vol. 22, p. 2670-2677.
Notomi et al, Nucleic Acids Res., 2000, vol. 28, p. e63.
Nagamine et al., Mol. Cell. Probes, 2002, vol. 16, p. 223-229.
Savan et al., Appl. Environ. Microbiol., 2004, vol. 70, p. 621-624.
Gunimaladevi et al., Arch. Virol., 2005, vol. 150, p. 899-909.
Yang et al., Microfluid. Nanofluid., 2006, vol. 6, p. 823-833.
Hsieh et al., Microfluid. Nanofluid., 2009, vol. 6, p. 797-809.
Hawkins et al., Nucleic Acids Res., 1994, vol. 22, p. 4543-4544.
Wang et al., Biosens Bioelectron., 2010, vol. 26(5), p. 2045-2052.

* cited by examiner

*Primary Examiner* — Christopher M Babic
*Assistant Examiner* — Aaron Priest
(74) *Attorney, Agent, or Firm* — WPAT, P.C.; Anthony King; Kay Yang

(57) ABSTRACT

The invention provides a method for rapidly detecting a pathogen in fish comprising conducting loop-mediated isothermal amplification with a specific primer set and a nucleic acid in a test sample. If at least one amplification is carried out, the test sample comprises the pathogen in fish. The invention also provides a primer set, probe and kit for detecting a pathogen in fish.

21 Claims, 3 Drawing Sheets

SEQUENCE LISTING

```
<160> NUMBER OF SEQ ID NOS: 28

<210> SEQ ID NO 1
<211> LENGTH: 18
<212> TYPE: DNA
<213> ORGANISM: Artificial Sequence
<220> FEATURE:
<223> OTHER INFORMATION: primer

<400> SEQUENCE: 1
ttggcaatgt agcacccg                                                 18

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
aagaacaagg ccttcacgg                                                19

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
agactgggcc accacctcac gtctgtgatg ggcacttac                          39

<210> SEQ ID NO 4
<211> LENGTH: 41
<212> TYPE: DNA
<213> ORGANISM: Artificial Sequence
<220> FEATURE:
<223> OTHER INFORMATION: primer

<400> SEQUENCE: 4
tcattgaaca gtgccaggtg gcaggtccag atgcaccaaa g                       41
```

-continued

```
<210> SEQ ID NO 5
<211> LENGTH: 30
<212> TYPE: DNA
<213> ORGANISM: Artificial Sequence
<220> FEATURE:
<223> OTHER INFORMATION: probe

<400> SEQUENCE: 5 ttttttttt gggaatgggc aaattaaggt                                       30

<210> SEQ ID NO 6
<211> LENGTH: 19
<212> TYPE: DNA
<213> ORGANISM: Artificial Sequence
<220> FEATURE:
<223> OTHER INFORMATION: primer

<400> SEQUENCE: 6
cgatcaacga cagcgacac                                                  19

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
gacagagagg tggtggtaga                                                 20

<210> SEQ ID NO 8
<211> LENGTH: 42
<212> TYPE: DNA
<213> ORGANISM: Artificial Sequence
<220> FEATURE:
<223> OTHER INFORMATION: primer

<400> SEQUENCE: 8
ccttctcgct caggccatag gtgttatgat gtcaccctgc gt                        42

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
tcaagtggcc attggtaggg ggatgcccag gactggttg                            39

<210> SEQ ID NO 10
<211> LENGTH: 30
<212> TYPE: DNA
<213> ORGANISM: Artificial Sequence
<220> FEATURE:
<223> OTHER INFORMATION: probe

<400> SEQUENCE: 10 ttttttttt agatcgcaaa gttgctgacc                                       30

<210> SEQ ID NO 11
<211> LENGTH: 18
<212> TYPE: DNA
<213> ORGANISM: Artificial Sequence
<220> FEATURE:
<223> OTHER INFORMATION: primer

<400> SEQUENCE: 11
```
caaagaacgc gttgaact                                                    18

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
gacgagcata tttgctacg                                                   19

<210> SEQ ID NO 13
<211> LENGTH: 50
<212> TYPE: DNA
<213> ORGANISM: Artificial Sequence
<220> FEATURE:
<223> OTHER INFORMATION: primer

<400> SEQUENCE: 13
gcaggtaagc agtgtaagaa gataatcttc aaccatatca agtaaacatg                 50

<210> SEQ ID NO 14
<211> LENGTH: 47
<212> TYPE: DNA
<213> ORGANISM: Artificial Sequence
<220> FEATURE:
<223> OTHER INFORMATION: primer

<400> SEQUENCE: 14
ccatgataca aataccgttt atggcgactt catcagtaac ttccatt                    47

<210> SEQ ID NO 15
<211> LENGTH: 30
<212> TYPE: DNA
<213> ORGANISM: Artificial Sequence
<220> FEATURE:
<223> OTHER INFORMATION: probe

<400> SEQUENCE: 15
tttttttttt tggctaaaac cacggaattc                                       30

<210> SEQ ID NO 16
<211> LENGTH: 18
<212> TYPE: DNA
<213> ORGANISM: Artificial Sequence
<220> FEATURE:
<223> OTHER INFORMATION: primer

<400> SEQUENCE: 16
tccgcgggtt acctgtac                                                    18

<210> SEQ ID NO 17
<211> LENGTH: 18
<212> TYPE: DNA
<213> ORGANISM: Artificial Sequence
<220> FEATURE:
<223> OTHER INFORMATION: primer

<400> SEQUENCE: 17
cgccgtcacc tgcttgaa                                                    18

<210> SEQ ID NO 18
<211> LENGTH: 41
<212> TYPE: DNA
<213> ORGANISM: Artificial Sequence

```
<220> FEATURE:
<223> OTHER INFORMATION: primer

<400> SEQUENCE: 18
tcggggaaga actgtccctc gtgaggtgat gcagcgtctg g                          41

<210> SEQ ID NO 19
<211> LENGTH: 41
<212> TYPE: DNA
<213> ORGANISM: Artificial Sequence
<220> FEATURE:
<223> OTHER INFORMATION: primer

<400> SEQUENCE: 19
ctacgaggga gtcgtgcagc tggggctgct gcataaagtc c                          41

<210> SEQ ID NO 20
<211> LENGTH: 30
<212> TYPE: DNA
<213> ORGANISM: Artificial Sequence
<220> FEATURE:
<223> OTHER INFORMATION: probe

<400> SEQUENCE: 20
tttttttttt acctcgcgat taagtggttg                                       30

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
ggcagcaaac agtctggcta                                                  20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
cggtgggtga cgttctttac                                                  20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
ggcggttgtg aggggttatc                                                  20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ggatgggtat accaggcatt                                                  20
```

```
<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
caattgacct aggcgctcat                                           20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tcacccatcg atacccagac                                           20

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
gatctccttc tccaccgtga                                           20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
agaggtcggg gaagaactgt                                           20
```

PRIMER SET, METHOD AND KIT FOR DETECTING PATHOGEN IN FISH

BACKGROUND OF THE INVENTION

1. Field of the Invention

The invention relates to a fish pathogen detection, and more particularly, to a fish pathogen detection using a loop-mediated isothermal amplification (LAMP) system.

2. Description of the Related Art

The detection of a nucleic acid fragment is widely used in various fields and important. For example, the rapid and accurate detection of a target nucleic acid fragment can be applied for quickly diagnosing a pathogen and is benefit for early prevention.

Rapid and accurate diagnosis leading to the quarantine of aqua-culture diseases has played a crucial part in protecting fisheries. Especially, the rapid identification of infectious diseases for species with a high economic value (e.g. grouper, eel or porgy) has attracted considerable interest in recent years. However, the immune system of a fish may be cross-infected by a variety of pathogens such as viruses, bacteria, fungi or parasites in various stages of development. Hence, the development of rapid, accurate, and sensitive diagnostic platforms for the identification of pathogens have played a fundamental role in treating, controlling, or even eradicating these infectious aquaculture diseases. Traditionally, several methods including bacteriological analysis, virus isolation and culture, histopathology and an enzyme-linked immunosorbent assay (ELISA) (Adams and Thompson, 2008, Rev. Sci. Technol. 27, 197-209) have been developed for the phenotypic characterization and resulting identification of these aquaculture pathogens. For example, viral nervous necrosis is a serious viral disease in the grouper cultivation industry. Many stages in the grouper life cycle can be infected with NNV, especially in hatchery-reared larvae and juveniles (Chi et al., 2003, Dis. Aquat. Organ. 55, 221-228). The NNV has been reported to be a major cause of mortality in the larvae and juveniles of farmed marine fish throughout the world (Shieh and Chi, 2005, Dis. Aquat. Organ. 63, 53-60). The necrosis and vacuolation of central nervous tissues result in abnormal swimming behavior in the infected species, which leads to a high mortality rate in infected fishes. The infected grouper may become a carrier and an outbreak may spread quickly if the quarantine is not imposed. There is a great need for a rapid and accurate diagnostic method for the prevention and control of this disease.

Alternatively, molecular diagnosis based on polymerase chain reaction (PCR), RT-PCR, (Dhar et al., 2002, J. Virol. Methods 104, 69-82; Nishizawa et al., 1995, J. Gen. Virol. 76, 1563-1569) or quantitative real-time PCR (DallaValle et al., 2005, Vet. Microbiol. 110, 167-179) incorporated with specific primer sets for nucleic acid amplification has been demonstrated for accurate diagnosis of aquaculture diseases with a high sensitivity and specificity. The current "gold-standard method" for detection of NNV uses a conventional RT-PCR method (Nishizawa et al., 1995, J. Gen. Virol. 76, 1563-1569). The detection limit of 100-1000 copies of in vitro transcribed viral RNA in the RT-PCR assay has been demonstrated (Grotmol et al., 2000, Dis. Aquat. Organ. 39, 79-88).

However, there still exist some disadvantages, such as the need for an expensive and bulky thermal cycler, multiple and complex operating processes and low amplification efficiency (Mori et al., 2001, Biochem. Biophys. Res. Commun. 289, 150-154; Tomita et al., 2008, Nat. Protoc. 3, 877-882). Furthermore, test sample pre-treatment still remains a technically demanding and time-consuming step. The quality of RNA extraction could affect the results of the RNA-virus diagnosis. A hot phenol extraction or RNA purification kits are common methods for RNA purification and separation. In addition, the requirements for PCR-based platforms are technically demanding such as the precise temperature control necessary during the thermal cycling with the temperature variation ranging from 42° C. to 95° C., which is commonly performed by costly and bulky apparatus. In addition, the lengthy and costly diagnostic processes always need to be performed by well-trained personnel and the inaccuracy of the diagnosis may be attributed to these manual operations.

Accordingly, "isothermal amplification techniques," which allow exponential amplification of target nucleic acids at a constant and low temperature, has been developed for rapid detection of target DNA sequences (Piepenburg et al., 2006, PLoS Biol. 4, e204; Starkey et al., 2004, Dis. Aquat. Organ. 59, 93-100; Walker et al., 1994, Nucleic Acids Res. 22, 2670-2677). Among them, the loop-mediated-isothermal-amplification (LAMP) technique has attracted considerable interests as a potentially rapid, accurate, and cost-effective method for nucleic acid amplification. Specific nucleic acid sequences in the target test samples can be amplified by using four designated primers with the incorporation of Bst DNA polymerase, which is capable of high strand displacement under isothermal conditions (about 60° C.-65° C.) (Notomi et al., 2000, Nucleic Acids Res. 28, e63). Three major steps including an initial step, a cycling amplification step and an elongation step are conducted under a constant thermal condition and efficient amplification can be achieved since there is no time required for temperature ramping during the LAMP process (Nagamine et al., 2002, Mol. Cell. Probes 16, 223-229). In addition, the final amplified stem-loop DNAs consisting of cauliflower-like structures with multiple loops yields an amplification of $10^9$ copies of target DNA molecules, so that approximately a 100-fold greater sensitivity for LAMP amplification is demonstrated when compared with a conventional PCR process. As a consequence, a new diagnostic strategy incorporated the LAMP technique for fast and accurate detection of target genes has been demonstrated. For example, a LAMP-based detection of *Edwardsiella tarda* from infected Japanese flounder has been reported by targeting the haemolysin gene (Savan et al., 2004, Appl. Environ. Microbiol. 70, 621-624). Another two-step RT-LAMP protocol for identification of the G-protein associated with the infectious haematopoietic necrosis virus (IHNV) in fish was also developed (Gunimaladevi et al., 2005, Arch. Virol. 150, 899-909). Despite the attractiveness of the LAMP technique, there are still some potential drawbacks in developing rapid diagnostic devices utilizing these state-of-the-art laboratory techniques. The entire nucleic acid amplification process is still costly and labor-intensive which utilizes lab-scale equipment such as pipettes and bulky thermo-heaters with a relatively large amount of bio-test samples/reagents. More importantly, bio-test sample pre-treatment processes prior to analysis such as DNA/RNA extraction are always required and need to be performed by experienced personnel. Furthermore, there is a high risk of contamination of bio-test samples during the entire diagnostic process, which may hinder the practical applications in the field survey.

Therefore, there is a great need to develop an integrated test sample-to-answer system to carry out all the diagnostic processes with a high specificity and sensitivity, in an automatic manner

SUMMARY OF THE INVENTION

The present invention provides an integrated microfluidic LAMP system for rapidly detecting a pathogen in fish.

The invention provides a primer set for loop-mediated isothermal amplification, which is selected from the group consisting of a first primer set, a second primer set, a third primer set, and a fourth primer set, wherein:

the first primer set comprises primers comprising the sequences of SEQ ID NOS: 1 to 4 or the complementary sequences thereof; the second primer set comprises primers comprising the sequences of SEQ ID NOS: 6 to 9 or the complementary sequences thereof; the third primer set comprises primers comprising the sequences of SEQ ID NOS: 11 to 14 or the complementary sequences thereof; and the fourth primer set comprises primers comprising the sequences of SEQ ID NOS: 16 to 19 or the complementary sequences thereof.

The invention also provides a probe selected from the group consisting of SEQ ID NOS: 5, 10, 15, and 20, or the complementary sequences thereof.

The invention also provides a method for detecting a pathogen in fish, which comprises conducting loop-mediated isothermal amplification with at least one primer set as mentioned above and a nucleic acid in a test sample, and if at least one amplification is carried out, the test sample comprises the pathogen in fish.

The invention also provides a kit for detecting a pathogen in fish comprising the primer set as mentioned above.

BRIEF DESCRIPTION OF THE DRAWINGS

FIG. 2(c) shows the detection limit of the present invention. The LAMP is conducted with the use of the reaction mixture listed in Table 2 at the isothermal temperature of 60° C. L lane: 100 bp DNA ladder marker; N lane: ddH$_2$O; lanes 1 to 9: 10-fold dilution of the sample (cloned positive control). The highest concentration is 10 µg/1 µL.

DETAILED DESCRIPTION OF THE INVENTION

Figure 1:
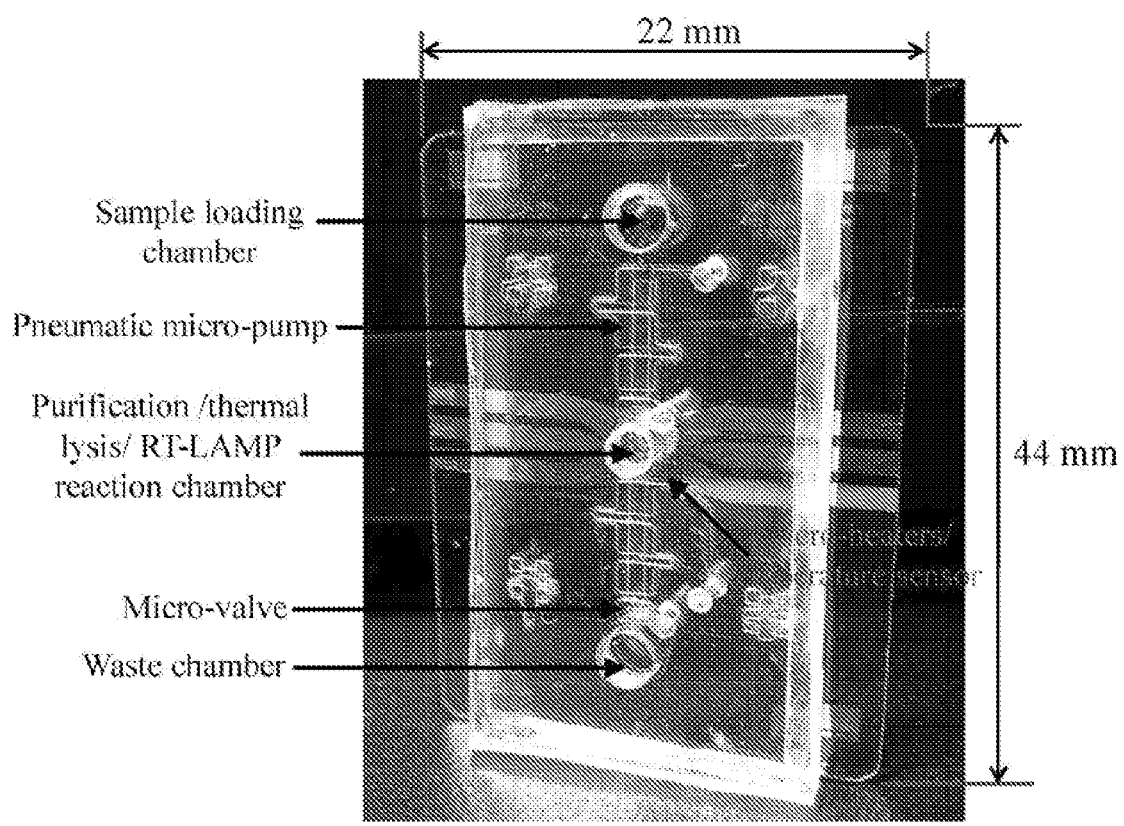
FIG. 1 illustrates a photograph of the integrated microfluidic LAMP system integrated with a microfluidic control module and the nucleic acid amplification module. The dimensions of the microfluidic chip are measured to be 44 mm×22 mm.

The invention provides a primer set for loop-mediated isothermal amplification, which is selected from the group consisting of a first primer set, a second primer set, a third primer set, and a fourth primer set, wherein:

the first primer set comprises primers comprising the sequences of SEQ ID NOS: 1 to 4 or the complementary sequences thereof; the second primer set comprises primers comprising the sequences of SEQ ID NOS: 6 to 9 or the complementary sequences thereof; the third primer set comprises primers comprising the sequences of SEQ ID NOS: 11 to 14 or the complementary sequences thereof; and the fourth primer set comprises primers comprising the sequences of SEQ ID NOS: 16 to 19 or the complementary sequences thereof.

As utilized in accordance with the present disclosure, the following terms, unless otherwise indicated, shall be understood to have the following meanings.

The term "oligonucleotide" as referred to herein means single-stranded or double-stranded nucleic acid polymers of at least 10 bases in length. In certain embodiments, the nucleotides comprising the oligonucleotide can be ribonucleotides or deoxyribonucleotides or a modified form of either type of nucleotide. Said modifications include base modifications such as bromuridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "oligonucleotide" specifically includes single and double stranded forms of DNA.

Often, ranges are expressed herein as from "about" one particular value and/or to "about" another particular value. When such a range is expressed, an embodiment includes the range from the one particular value and/or to the other particular value. Similarly, when values are expressed as approximations, by use of the word "about," it will be understood that the particular value forms another embodiment. It will be further understood that the endpoints of each of the ranges are significant both in relation to and independently of the other endpoint.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "the complementary sequence" as used herein refers to a nucleic acid molecule able to be hybridized to the primer or probe according to the invention; preferably, refers to a nucleic acid molecule able to be completely hybridized to the primer or probe according to the invention.

The first primer set according to the invention is designed according to major capsid protein of *Iridovirus*. More specifically, the major capsid protein is encoded by Genbank accession Nos. AY285745 and AY989901. SEQ ID NO: 1 is a forward primer of an outer primer pair; SEQ ID NO: 2 is a reversed primer of the outer primer pair; SEQ ID NO: 3 is a forward primer of an inner primer pair; and SEQ ID NO: 4 is a reversed primer of the inner primer pair.

The second primer set according to the invention is designed according to hemolysin of *Aeromonas hydrophila*. More specifically, the hemolysin is encoded by Genbank accession No. AB021152. SEQ ID NO: 6 is a forward primer of an outer primer pair; SEQ ID NO: 7 is a reversed primer of the outer primer pair; SEQ ID NO: 8 is a forward primer of an inner primer pair; and SEQ ID NO: 9 is a reversed primer of the inner primer pair.

The third primer set according to the invention is designed according to ornithine carbamoyltransferase of *Streptococcus agalactiae*. More specifically, the ornithine carbamoyltransferase is encoded by Genbank accession No. AF439647. SEQ ID NO: 11 is a forward primer of an outer primer pair; SEQ ID NO: 12 is a reversed primer of the outer primer pair; SEQ ID NO: 13 is a forward primer of an inner primer pair; and SEQ ID NO: 14 is a reversed primer of the inner primer pair.

The fourth primer set according to the invention is designed according to thymidine kinase of koi herpes virus. More specifically, the thymidine kinase is encoded by Genbank accession No. AJ535112. SEQ ID NO: 16 is a forward primer of an outer primer pair; SEQ ID NO: 17 is a reversed primer of the outer primer pair; SEQ ID NO: 18 is a forward primer of an inner primer pair; and SEQ ID NO: 19 is a reversed primer of the inner primer pair.

The primer set according to the invention can be applied in loop-mediated isothermal amplification to detection the existence of a pathogen in fish, and the kind of the pathogen in fish can be further identified and disease control and prevention are provided early.

Each of the inner primer pair and outer primer pair of the first primer set, second primer set, third primer set, and fourth primer set according to the invention can be reacted under one condition, and no cross reactions occur between each other, and the sensitivity and specificity are both high.

In one preferred embodiment of the invention, hybridization and loop-mediated isothermal amplification can be applied simultaneously for detecting a pathogen in fish more rapidly and accurately.

Therefore, the invention also provides a probe selected from the group consisting of SEQ ID NOS: 5, 10, 15, and 20, or the complementary sequences thereof.

The probe encoded by SEQ ID NO: 5 according to the invention is designed according to major capsid protein of *Iridovirus*. More specifically, the major capsid protein is encoded by Genbank accession Nos. AY285745 and AY989901.

The probe encoded by SEQ ID NO: 10 according to the invention is designed according to hemolysin of *Aeromonas hydrophila*. More specifically, the hemolysin is encoded by Genbank accession No. AB021152.

The probe encoded by SEQ ID NO: 15 according to the invention is designed according to ornithine carbamoyltransferase of *Streptococcus agalactiae*. More specifically, the ornithine carbamoyltransferase is encoded by Genbank accession No. AF439647.

The probe encoded by SEQ ID NO: 20 according to the invention is designed according to thymidine kinase of koi herpes virus. More specifically, the thymidine kinase is encoded by Genbank accession No. AJ535112.

The principle of probe design is the location sequence of the probe having infrequent variation occurred, and:
1. the length of the probe is preferred between 17 to 27 nucleotides, and if the probe is too short, it causes a difficult target DNA binding; if the probe is too long, non-specific hybridization occurs easily;
2. the G+C ratio is between 40% to 60% to lowered the probability of secondary structure;
3. the Tm (melting temperature) is designed as much as possible at the hybridization temperature ±5° C.; for example, if the hybridization temperature is designed at 50° C., the Tm of the probe should be as much as possible at 45° C. to 55° C.;
4. hairpin loops, palindrome, and repeats are avoided as much as possible;
5. a mismatch is designed in the middle position of the whole probe, and 8 and 10 thymines are added at the 3'-end of the probe to facilitate the binding between the probe and a nylon membrane.

A designed probe is subjected to BLAST to make sure that no sequence similarity with other species in GenBank for avoiding cross hybridization.

The term "a probe" as used herein refers to a nucleic acid molecule containing at least 8 consecutive nucleotides; preferably 10 to 50 consecutive nucleotides; more preferably 15 to 40 consecutive nucleotides; most preferably 17 to 27 consecutive nucleotides. In another aspect, 8 and 10 thymines are preferably contained at the 3'-end of the probe. The probe can be applied in hybridization under a hybridization condition with a target DNA. The hybridization condition can be set by artisans skilled in the field, and preferably between about 40° C. to about 65° C.

To sum up, the primer sets and probes according to the invention are listed in Table 1:

| SEQ ID No. | Name | Sequence |
|---|---|---|
| 1 | Iridovirus-F3 | TTGGCAATGTAGCACCCG |
| 2 | Iridovirus-B3 | AAGAACAAGGCCTTCACGG |
| 3 | Iridovirus-FIP | AGACTGGGCCACCACCTCACGTCTGTGATGGGCACTTAC |
| 4 | Iridovirus-BIP | TCATTGAACAGTGCCAGGTGGCAGGTCCAGATGCACCAAAG |
| 5 | Iridovirus-probe | TTTTTTTTTTGGGAATGGGCAAATTAAGGT |
| 6 | AH-F3 | CGATCAACGACAGCGACAC |
| 7 | AH-B3 | GACAGAGAGGTGGTGGTAGA |
| 8 | AH-FIP | CCTTCTCGCTCAGGCCATAGGTGTTATGATGTCACCCTGCGT |
| 9 | AH-BIP | TCAAGTGGCCATTGGTAGGGGGATGCCCAGGACTGGTTG |

-continued

| SEQ ID No. | Name | Sequence |
|---|---|---|
| 10 | AH-probe | TTTTTTTTTTAGATCGCAAAGTTGCTGACC |
| 11 | SA-F3 | CAAAGAACGCGTTGAACT |
| 12 | SA-B3 | GACGAGCATATTTGCTACG |
| 13 | SA-FIP | GCAGGTAAGCAGTGTAAGAAGATAATCTTCAACCATATCAAGTAAACATG |
| 14 | SA-BIP | CCATGATACAAATACCGTTTATGGCGACTTCATCAGTAACTTCCATT |
| 15 | SA-probe | TTTTTTTTTTGGCTAAAACCACGGAATTC |
| 16 | KHV-F3 | TCCGCGGGTTACCTGTAC |
| 17 | KHV-B3 | CGCCGTCACCTGCTTGAA |
| 18 | KHV-FIP | TCGGGGAAGAACTGTCCCTCGTGAGGTGATGCAGCGTCTGG |
| 19 | KHV-BIP | CTACGAGGGAGTCGTGCAGCTGGGGCTGCTGCATAAAGTCC |
| 20 | KHV-probe | TTTTTTTTTTACCTCGCGATTAAGTGGTTG |

The invention also provides a method for detecting a pathogen in fish, which comprises conducting loop-mediated isothermal amplification with at least one primer set as mentioned above and a nucleic acid in a test sample, and if at least one amplification is carried out, the test sample comprises the pathogen in fish.

In one preferred embodiment of the invention, the method is further used for detecting the kind of the pathogen in fish.

If the amplification is carried out with the nucleic acid in the test sample and the first primer set, the test sample comprises *Iridovirus*.

If the amplification is carried out with the nucleic acid in the test sample and the second primer set, the test sample comprises *Aeromonas hydrophila*.

If the amplification is carried out with the nucleic acid in the test sample and the third primer set, the test sample comprises *Streptococcus agalactiae*.

If the amplification is carried out with the nucleic acid in the test sample and the fourth primer set, the test sample comprises koi herpes virus.

The test sample according to the present invention may contain pathogenic culture to be identified, specimen from the diseased fish, or a sample of the nucleic acid information further derived from the pathogenic culture to be identified or specimen from the diseased fish; wherein the specimen from the diseased fish is preferably the blood, muscle or brain tissue.

In one preferred embodiment of the invention, the product of the loop-mediated isothermal amplification in the sample is marked. The manner of marking the product of the loop-mediated isothermal amplification is known to artisans skilled in the art. For example, when conducting the loop-mediated isothermal amplification, the primer comprises a marker, and preferably, the marker is digoxigenin, or a marked dUTP can be used for introducing a marker in the product.

In one preferred embodiment of the invention, the method further comprises a positive control step. Any determined primers for identifying a determined fragment are suitable for the positive control step.

In one preferred embodiment of the invention, the method further comprises conducting hybridization with at least one probe and the nucleic acid in the test sample, wherein the at least one probe is selected from the group consisting of SEQ ID NOS: 5, 10, 15, and 20, or the complementary sequences thereof.

In one preferred embodiment of the invention, the at least one probe is linked to a magnetic bead.

According to the invention, the magnetic bead and the at least one probe linked thereon are designed for purifying the nucleic acid in the test sample to facilitate the following operations. Artisans skilled in the field of the invention can choose an appropriate material and size of the magnetic bead. In one preferred embodiment of the invention, the diameter of the magnetic bead is from about 1 µm to about 5.0 µm. Such range both facilitates the linkage between the magnetic bead and the at least one probe and the following operations.

According to the invention, the manner for linking the at least one probe to the magnetic bead is well-known to artisans skilled in the field of the invention according to the disclosure of the specification of the invention. A conventional manner of linking an oligonucleotide to a magnetic bead can be applied in the invention. In one preferred embodiment of the invention, the magnetic bead is linked to the at least one probe through an amide bond or a carboxylate bond.

According to the invention, the at least one probe is designed for hybridizing the pathogenic nucleic acid in the test sample through a complementary feature. The hybridizing complex is further purified by the magnetic force. Moreover, the two hybridized strands can be separated in the subsequently loop-mediated isothermal amplification, and further amplified.

According to the invention, the reagents for loop-mediated isothermal amplification are well-known to artisans skilled in the field of the invention according to the disclosure of the specification of the invention. For example, the design described in Notomi et al, 2000, Nucleic Acids Res. 28, e63. Such disclosure is incorporated herein by reference.

In one preferred embodiment of the invention, the nucleic acid in the test sample is a RNA fragment, and the method further comprises conducting a reverse transcription polymerase chain reaction. It allows carrying on the reverse transcription polymerase chain reaction before the purification and amplification.

In one preferred embodiment of the invention, the method comprises the steps of:

(a) purifying the nucleic acid in the test sample with a magnetic bead;

(b) conducting loop-mediated isothermal amplification with the primer set and the nucleic acid in the step (a); and (c) detecting a product of the loop-mediated isothermal amplification.

The invention also provides a kit for detecting a pathogen in fish comprising the primer set as mentioned above.

In one preferred embodiment of the invention, the kit further comprises at least one probe as mentioned above.

In one preferred embodiment of the invention, the kit further comprises a magnetic bead, and the magnetic bead is linked to the at least one probe.

In one preferred embodiment of the invention, the kit further comprises reagents for loop-mediated isothermal amplification.

In one preferred embodiment of the invention, the kit further comprises reagents for a reverse transcription polymerase chain reaction. It allows carrying on a reverse transcription polymerase chain reaction before the purification and amplification.

In one preferred embodiment of the invention, the kit further comprises a microfluidic chip. As used herein, "a microfluidic chip" refers to an apparatus that detection-required elements such as a test sample loading chamber, a pneumatic micro-pump, a reaction chamber, a micro-valve, and a waste chamber, are integrated thereon. The test sample or reagents are driven to move in micro-channels connecting the elements by electroosmotic flow generated by voltage applied or the use of micro-pumps or a centrifugal force to complete the reaction. The microfluidic chip also known as a lab-on-a-chip, and the use of microfluidic chip for biomedical detection or analysis has advantages of reduced manual error, increased system stability, reduced energy consumption and reduced amount of test samples, reduced the capacity and time-saving.

In one preferred embodiment of the invention, the microfluidic chip comprises a microfluidic control module and an isothermal amplification module is shown in FIG. 1. The microfluidic control module comprises one glass substrate with metallization patterns and two polydimethylsiloxane (PDMS) layers, namely a thick PDMS layer with structures for the microfluidic channel and a thin-film PDMS membrane for the air chambers. The microfluidic control module further comprises one test sample loading chamber, one purification/thermal lysis/LAMP reaction chamber, a waste chamber and two sets of pneumatic micro-pumps with normally-closed micro-valves. These valves are designed for liquid delivery and to prevent backflow in the miniature system. The optimal design parameters, microfabrication and characterizations for the module can be referenced of Yang et al., 2009 (Yang et al., 2009, Microfluid. Nanofluid. 6, 823-833). Such disclosure is incorporated herein by reference.

The isothermal amplification module of the microfluidic chip preferably comprises two sets of self-compensated, array-type micro-heaters and a temperature sensor is built to generate the temperature distribution with a high thermal uniformity within the thermal lysis/LAMP reaction chamber. Without using additional control circuits, the isothermal amplification module is fabricated with surrounding heating grids which are used as compensating heaters for the edge areas. Hence, the amplification efficiency of the LAMP process can be enhanced within the reaction chamber distributed with a high thermal uniformity. Details of the self-compensated, isothermal amplification module and the microfabrication process can be found in the previous literature (Hsieh et al., 2009, Microfluid. Nanofluid. 6, 797-809). Meanwhile, in one preferred embodiment of the invention, an application specific integrated circuit (ASIC) controller is used to control all the components including the microfluidic control module and the isothermal amplification module. A heat sink with a pocket for placement of a permanent magnet and an adjustable magnetic stage directly connected to a compressed gas tank regulated by the EMV are employed. The permanent magnet on the magnetic stage can be engaged and slided into the pocket automatically during the purification process by providing a digital signal into the EMV, followed by disengaging it from the pocket during the re-suspension and LAMP processes. Thus, the test sample transportation process and the temperature field distribution can be precisely and automatically controlled.

Preferably, the kit according to the invention further comprises an apparatus or a system for detecting the product of the amplification. In one preferred embodiment of the invention, the kit further comprises a gel electrophoresis system or an absorbance detection system for detecting a product of loop-mediated isothermal amplification.

In one preferred embodiment of the invention, in the amplification processes within LAMP, pyrophosphate is released, followed with nucleic acid elongation, and is reacted with magnesium ions to cause a change in turbidity in the mixture. Consequently, an optical system is integrated in the future to sense the turbidity variation for the amount of end product.

In one preferred embodiment of the invention, the kit further comprises a lysis buffer for lysing the test sample. More preferably, the lysis buffer is able to preliminarily lysing the test sample to facilitate the following purification and amplification.

In one preferred embodiment of the invention, the method provides the specific primer sets and probes for detecting *Iridovirus, Aeromonas hydrophila, Streptococcus agalactiae*, and koi herpes virus, the four common pathogens in fish. First, the probe specific to the pathogen is linked to the magnetic bead. After lysing the cells, the pathgenic nucleic acids dissolved in the whole-tissue lysate in the test sample are specifically detected and hybridized on the surface of the magnetic bead. Hereafter, the combination of the built-in microfluidic control module and permanent magnet is applied to purify the magnetic complex from the test sample. In addition, the one-step isothermal LAMP is performed to amplify the target gene by the use of the isothermal amplification module of the chip. Thus, the kit and method according to the present invention provides an automated platform of a fast diagnosis of disease in aquaculture with little need of human intervention. The duration from extracting the nucleic acid to obtain the result is only 65 minutes, and the waiting time is significantly reduced. With this combination of the specific probes and the magnetic beads, the pathogenic nucleic acid can be captured directly, and the extraction and purification of nucleic acid are simplified. In another aspect, the primer set according to the invention can isothermally amplify the pathogenic nucleic acid, and is proven to have high specificity.

The minimum detection limit of the present invention can be lowered to 20 copies, that is about 1000 times higher than that of the conventional PCR, and the sensitivity is significantly increased. Furthermore, LAMP uses four primers to react, so that the specificity is higher than that of the conventional PCR, and the error rate is significantly reduced. Therefore, the method and kit according to the invention can be used for early detection to protect the species with a high economic value.

The following Examples are given for the purpose of illustration only and are not intended to limit the scope of the present invention.

EXAMPLE

Experimental Procedures

The microfluidic chip shown in FIG. 1 is applied in the example. The nucleic acids of the *Iridovirus, Aeromonas hydrophila, Streptococcus agalactiae*, and koi herpes virus infected fishes are isolated by utilizing probe-conjugated magnetic beads, followed by performing the one-step isothermal amplification with the incorporation of built-in microheaters and temperature sensors. Briefly, a random sampling of Koi, grouper or tilapia is first carried out in the fishery, followed by a grinding process with a pestle in an 1.5 mL microcentrifuge tube. The on-chip micro-heaters are then activated to perform the thermal lysis of the bio-test samples when the tissue fluid of the fishes is loaded into a purification chamber of the microfluidic chip.

Then, the hybridization of the released nucleic acids is performed by loading the specific probe-conjugated, magnetic beads into the purification chamber at 58° C. Next, a permanent magnet is attached underneath the chip to attract the hybridized nucleic acid-probe-conjugated magnetic complexes onto the surface of the purification chamber, followed by flowing a washing buffer through the purification chamber continuously using an integrated micro-pump. All the other unbound interferents in the biological solution would then be washed away into a waste chamber. The LAMP reagents are then loaded into a test sample loading chamber, followed by transporting them into the purification chamber to perform the subsequent synthesization of target gene and isothermal amplification simultaneously. With this approach, the pathogenic nucleic acid can be isolated from the biological tissues and then are used in the subsequent identification of genetic patterns associated with aquaculture diseases.

Detailed procedure is illustrated below.

Infectious Fish Test Samples Preparation

The *Iridovirus, Aeromonas hydrophila, Streptococcus agalactiae*, and koi herpes virus infected Koi, grouper or tilapia are first sampled randomly and collected from cultivation farms. All the fish samples, including the brain and other tissues, are stored at −80° C. prior to the pathogenic nucleic acid extraction process and the on-chip analysis. To avoid the clogging of the micro channels by large or tough fish tissue, the fish organs are grinded using a tissue grinder to obtain virus particles from extracted test samples.

Probe and Primers Design

The primers and probes are designed by selecting major capsid protein of *Iridovirus* (AY285745 and AY989901), hemolysin of *Aeromonas hydrophila* (AB021152), ornithine carbamoyltransferase of *Streptococcus agalactiae* (AF439647), and thymidine kinase of koi herpes virus (AJ535112) using Eiken Genome site (http://primerexplorer.jp/elamp3.0.0/index.html) and Primer3 (http://frodo.wi.mit.edu/primer3/). The sequences are listed in Table 1.

Magnetic Bead-Based RNAJ Extraction and Hybridization

A specific probe is conjugated onto the surface of the magnetic beads (MAGBEAD AGT-003-05, Applied gene technologies technologies, USA) by utilizing the carboxylated linkage prior to the on-chip analysis (Hawkins et al., 1994, Nucleic Acids Res. 22, 4543-4544). A grinding process is first performed by using a pestle with a 200 μL of lysis buffer [62.5 mM Tris, pH8.3, 95 mM KCl, 3.8 mM $MgCl_2$, 12.5 mM dithiothreitol (DTT), and 0.63% octyl phenoxylpoly ethoxylethanol (NP-40)] in an 1.5 mL microcentrifuge tube to collect the whole tissue lysates. Then, 25 μL of whole tissue lysates is then loaded into the purification chamber, where the pathogenic nucleic acid-specific probe-conjugated magnetic beads with a volume of 10 μL are pre-loaded, to perform the thermal lysis process of the virus at 90° C. to 97° C. for 5 to 10 min. After that, a temperature field of 55° C. to 65° C. for 15 min is generated within the purification chamber for the hybridization process between the pathogenic nucleic acid and the specific probe-conjugated magnetic beads. Then, a magnetic field (~300 Gauss) generated by a permanent magnet is used to concentrate and to collect the nucleic acid-bound magnetic complexes onto the surface of the purification chamber, followed by washing all the other biological substances away into the waste chamber with the incorporation of micro-pumps and micro-valves. Next, the LAMP reagents are introduced into the reaction for the subsequent one-step LAMP process by the micro-pumps One-Step LAMP A final reaction volume of 25 μL is employed for the one-step RT-LAMP process and the LAMP reaction is modified as previously described (Notomi et al., 2000, Nucleic Acids Res. 28, e63). The reaction mixture is listed in Table 2.

TABLE 2

| mixture | Volumn (μL) |
|---|---|
| 10x reaction buffer | 2.5 |
| dNTP (2.5 μM) | 2.8 |
| Outer primer pair (10 μM/primer) | |
| B3 | 0.9 |
| F3 | 0.9 |
| Inner primer pair (20 μM/primer) | |
| BIP | 0.9 |
| FIP | 0.9 |
| Bst DNA polymerase | 1 |
| $ddH_2O$ | 15.1 |
| Total | 25 |

The reaction mixture is loaded in the LAMP reaction chamber for the isothermal amplification at 60° C. The LAMP products are analyzed by slab-electrophoresis technique in a 2% agarose gel.

In addition, in order to ensure accuracy of the present invention, a negative control of using $ddH_2O$ instead of the sample and a positive control of the primer sets listed in Table 3 cloned into pCR® 2.1-TOPO® are also provided.

TABLE 3

| SEQ ID No. | Primer | Sequence |
|---|---|---|
| 21 | Iridovirus-F | GGCAGCAAACAGTCTGGCTA |
| 22 | Iridovirus-B | CGGTGGGTGACGTTCTTTAC |
| 23 | AH-F | GGCGGTTGTGAGGGGTTATC |
| 24 | AH-B | GGATGGGTATACCAGGCATT |
| 25 | SA-F | CAATTGACCTAGGCGCTCAT |
| 26 | SA-B | TCACCCATCGATACCCAGAC |
| 27 | KHV-F | GATCTCCTTCTCCACCGTGA |
| 28 | KHV-B | AGAGGTCGGGGAAGAACTGT |

Figure 2:
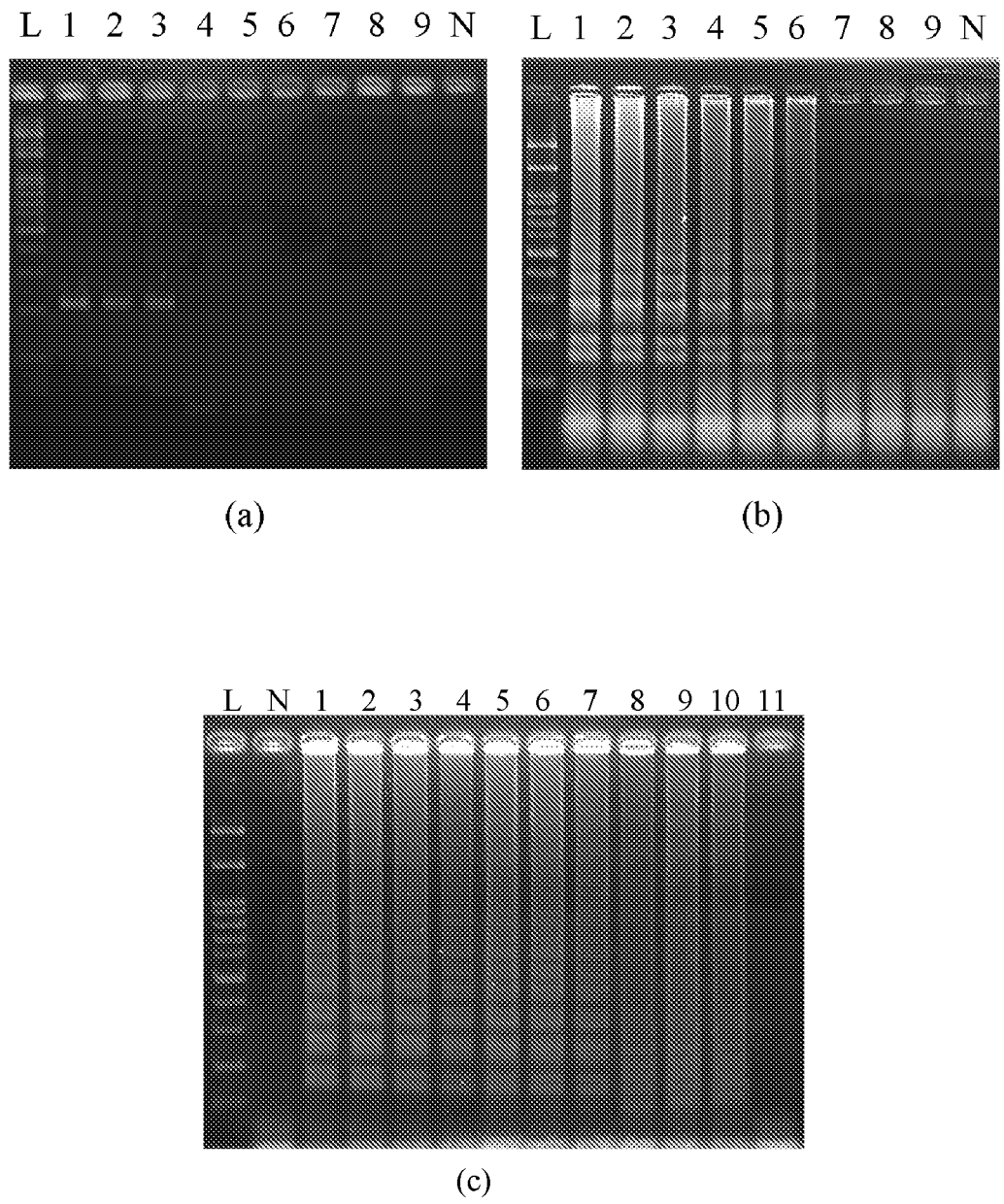
FIGS. 2 (a) and (b) show the comparison of the method according to the invention and the conventional PCR. (a) The conventional PCR is conducted with the outer primers of LAMP. The condition is 95° C. for 5 minutes; 95° C. for 30 seconds, 56° C. for 30 seconds, 72° C. for 30 seconds for 35 cycles; 72° C. for 7 minutes. (b) The LAMP is conducted with the use of the reaction mixture listed in Table 2 at the isothermal temperature of 60° C. L lane: 100 bp DNA ladder marker; N lane: ddH$_2$O; lanes 1 to 9: 10-fold dilution of the sample (genomic DNA of the grouper infected by *Iridovirus*). The highest concentration is 50 µg/1 µL.

FIGS. 2 (a) and (b) show the comparison of the method according to the invention and the conventional PCR. (a) The conventional PCR is conducted with the outer primers of LAMP. The condition is 95° C. for 5 minutes; 95° C. for 30 seconds, 56° C. for 30 seconds, 72° C. for 30 seconds for 35 cycles; 72° C. for 7 minutes. (b) The LAMP is conducted with the use of the reaction mixture listed in Table 2 at the isothermal temperature of 60° C. L lane: 100 bp DNA ladder marker; N lane: ddH$_2$O; lanes 1 to 9: 10-fold dilution of the sample (genomic DNA of the grouper infected by *Iridovirus*). The highest concentration is 50 µg/1 µL. The results show that the sensitivity of the present invention is 1000 times higher than that of the conventional PCR (Iridovirus example). FIG. 2(c) shows the detection limit of the present invention. The LAMP is conducted with the use of the reaction mixture listed in Table 2 at the isothermal temperature of 60° C. L lane: 100 bp DNA ladder marker; N lane: ddH$_2$O; lanes 1 to 9: 10-fold dilution of the sample (cloned positive control). It shows that the minimum detection limit of the method according to the invention is 0.001 fg; that corresponds to 20 copies.

Figure 3:
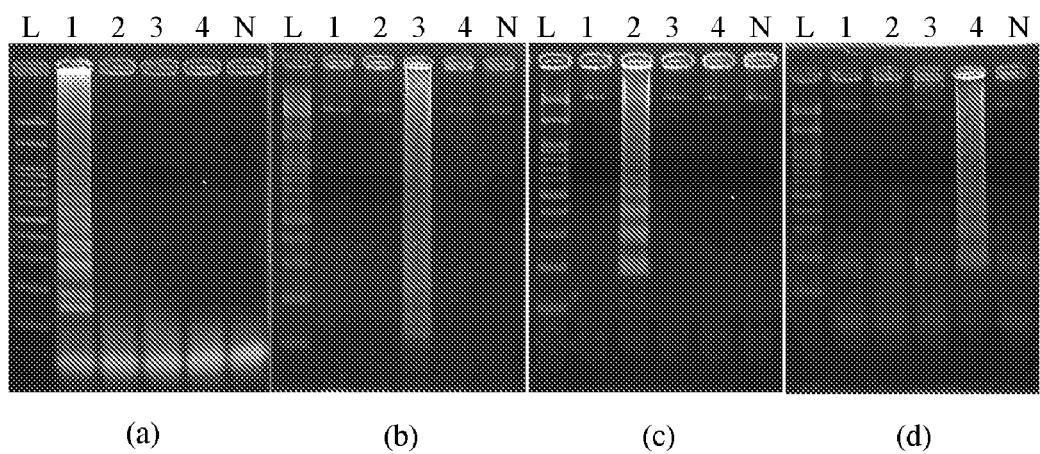
FIG. 3 shows the specificity of the method according to the invention. The LAMP is conducted with the use of the reaction mixture listed in Table 2 at the isothermal temperature of 60° C. L lane: 100 bp DNA ladder marker; N lane: ddH$_2$O; lane 1: genomic DNA of the fish infected by *Iridovirus*; lane 2: genomic DNA of the fish infected by *Streptococcus agalactiae*; lane 3: genomic DNA of the fish infected by koi herpes virus. (a) LAMP is conducted with the primer pair of *Iridovirus*. (b) LAMP is conducted with the primer pair of *Streptococcus agalactiae*. (c) LAMP is conducted with the primer pair of koi herpes virus. (d) LAMP is conducted with the primer pair of *Aeromonas hydrophila*.

FIG. 3 shows the specificity of the method according to the invention. The LAMP is conducted with the use of the reaction mixture listed in Table 2 at the isothermal temperature of 60° C. L lane: 100 bp DNA ladder marker; N lane: ddH$_2$O; lane 1: genomic DNA of the fish infected by *Iridovirus*; lane 2: genomic DNA of the fish infected by *Streptococcus agalactiae*; lane 3: genomic DNA of the fish infected by koi herpes virus. (a) LAMP is conducted with the primer pair of *Iridovirus*. (b) LAMP is conducted with the primer pair of *Streptococcus agalactiae*. (c) LAMP is conducted with the primer pair of koi herpes virus. (d) LAMP is conducted with the primer pair of *Aeromonas hydrophila*. It shows that the method according to the invention has the high specificity.

While embodiments of the present invention have been illustrated and described, various modifications and improvements can be made by persons skilled in the art. The present invention is not limited to the particular forms as illustrated, and that all the modifications not departing from the spirit and scope of the present invention are within the scope as defined in the appended claims.

What is claimed is:

1. A primer set for loop-mediated isothermal amplification, comprising:
   a first primer set comprising primers comprising the sequences of SEQ ID NOS: 11-14 or the complementary sequences thereof.

2. A method for detecting a pathogen in fish, which comprises conducting loop-mediated isothermal amplification with the first primer set according to claim 1 and a nucleic acid in a test sample, and if at least one amplification is carried out, the test sample comprises the pathogen in fish.

3. The method according to claim 2, which further comprises conducting hybridization with at least one probe and the nucleic acid in the test sample, wherein the at least one probe is selected from the group consisting of SEQ ID NOS: 5, 10, 15, and 20, or the complementary sequences thereof.

4. The method according to claim 3, wherein the at least one probe is linked to a magnetic bead.

5. The method according to claim 2, which further comprises conducting a reverse transcription polymerase chain reaction.

6. The method according to claim 2, which comprises the steps of:
   (a) purifying the nucleic acid in the test sample with a magnetic bead;
   (b) conducting loop-mediated isothermal amplification with the primer set and the nucleic acid in the step (a); and
   (c) detecting a product of the loop-mediated isothermal amplification.

7. The method according to claim 2, which comprises the steps of:
   (a) purifying the nucleic acid in the test sample with a magnetic bead;
   (b) conducting loop-mediated isothermal amplification with the primer set and the nucleic acid in the step (a); and
   (c) detecting a product of the loop-mediated isothermal amplification.

8. The method according to claim 3, which comprises the steps of:
   (a) purifying the nucleic acid in the test sample with a magnetic bead;
   (b) conducting loop-mediated isothermal amplification with the primer set and the nucleic acid in the step (a); and
   (c) detecting a product of the loop-mediated isothermal amplification.

9. The method according to claim 4, which comprises the steps of:
   (a) purifying the nucleic acid in the test sample with a magnetic bead;
   (b) conducting loop-mediated isothermal amplification with the primer set and the nucleic acid in the step (a); and
   (c) detecting a product of the loop-mediated isothermal amplification.

10. The method according to claim 5, which comprises the steps of:
    (a) purifying the nucleic acid in the test sample with a magnetic bead;
    (b) conducting loop-mediated isothermal amplification with the primer set and the nucleic acid in the step (a); and
    (c) detecting a product of the loop-mediated isothermal amplification.

11. A kit for detecting a pathogen in fish comprising the primer set according to claim 1.

12. The kit according to claim 11, which further comprises at least one probe selected from the group consisting of SEQ ID NOS: 5, 10, 15, and 20, or the complementary sequences thereof.

13. The kit according to claim 12, which further comprises a magnetic bead, and the magnetic bead is linked to the at least one probe.

14. The kit according to claim 11, which further comprises reagents for loop-mediated isothermal amplification.

15. The kit according to claim 11, which further comprises a microfluidic chip.

16. The kit according to claim 11, which further comprises a gel electrophoresis system or an absorbance detection system for detecting a product of loop-mediated isothermal amplification.

17. The kit according to claim 11, which further comprises a lysis buffer for lysing a test sample.

18. The primer set according to claim 1, which further comprises a second primer set comprising primers comprising the sequences of SEQ ID NOS: 1 to 4 or the complementary sequences thereof; a third primer set comprising primers comprising the sequences of SEQ ID NOS: 6 to 9 or the complementary sequences thereof; or a fourth primer set comprising primers comprising the sequences of SEQ ID NOS: 16 to 19 or the complementary sequences thereof.

19. The method according to claim 2, which further comprises conducting loop-mediated isothermal amplification with at least one of second primer set, third primer set and fourth primer set and the nucleic acid in the test sample; wherein the second primer set comprising primers comprising the sequences of SEQ ID NOS: 1 to 4 or the complementary sequences thereof; the third primer set comprising primers comprising the sequences of SEQ ID NOS: 6 to 9 or the complementary sequences thereof; the fourth primer set comprising primers comprising the sequences of SEQ ID NOS: 16 to 19 or the complementary sequences thereof.

20. The kit according to claim 11, which further comprises a second primer set comprising primers comprising the sequences of SEQ ID NOS: 1 to 4 or the complementary sequences thereof; a third primer set comprising primers comprising the sequences of SEQ ID NOS: 6 to 9 or the complementary sequences thereof; or a fourth primer set comprising primers comprising the sequences of SEQ ID NOS: 16 to 19 or the complementary sequences thereof.

21. The method according to claim 19, wherein:
    if the amplification is carried out with the nucleic acid in the test sample and the first primer set, the test sample comprises *Streptococcus agalactiae*; and
    if the amplification is carried out with the nucleic acid in the test sample and the second primer set, the test sample comprises *Iridovirus*;
    if the amplification is carried out with the nucleic acid in the test sample and the third primer set, the test sample comprises *Aeromonas hydrophila*; and
    if the amplification is carried out with the nucleic acid in the test sample and the fourth primer set, the test sample comprises koi herpes virus.

* * * * *